United States Patent [19]

Eckner et al.

[11] Patent Number: 5,616,499
[45] Date of Patent: Apr. 1, 1997

[54] CULTURE AND TRANSFER DEVICE FOR ENHANCED RECOVERY AND ISOLATION OF MICROORGANISMS

[75] Inventors: Karl F. Eckner; Elliot T. Ryser, both of Park Forest, Ill.; Richard B. Smittle, Stouchsburg, Pa.

[73] Assignee: Silliker Laboratories Group, Inc., Chicago Heights, Ill.

[21] Appl. No.: 326,181

[22] Filed: Oct. 19, 1994

Related U.S. Application Data

[62] Division of Ser. No. 990,572, Dec. 14, 1992, abandoned.

[51] Int. Cl.$^6$ ........................................................ C12M 1/00
[52] U.S. Cl. ................................... 435/309.1; 435/304.2; 435/309.2
[58] Field of Search ........................... 435/4, 30, 287, 435/292, 295, 296, 34, 309.1, 309.2, 309.4, 304.2, 305.2; 436/20; 128/760, 763, 759; 220/703, 713, 745, 212, 253, 254, 255, DIG. 32, DIG. 33; 422/56

[56] References Cited

U.S. PATENT DOCUMENTS

| | | | |
|---|---|---|---|
| 3,640,268 | 2/1972 | Davis | 128/759 |
| 3,815,580 | 6/1974 | Oster | 128/759 |
| 3,890,204 | 6/1975 | Avery | 435/292 |
| 4,376,634 | 3/1983 | Prior et al. | 435/292 |
| 4,643,825 | 2/1987 | Weslowski | 220/254 |
| 4,877,037 | 10/1989 | Ko et al. | 128/756 |
| 5,091,316 | 2/1992 | Monthony et al. | 435/295 |

OTHER PUBLICATIONS

Lennette, et al. Manual of Clinical Microbiology Third Edition American Society for Microbiology Wash DC. 1980 pp. 139–142, 195–219, 235–241.

Park, C.E., Smibert, R.M., Blaser, M.J., Vanderzant, C., "Campylobacter." in: *Indicator microorganisms and Pathogens*, chapter 31, (date unknown), pp. 386–404.

Ray, Bibek, Adams, Jr., D.M., "Repair and Detection of Injured Microorganisms." in: *General Laboratory Procedures*, chapter 7, (date unknown), pp. 112–123.

Costerton, J.W., Geesey G.G., Cheng, K.J., "How Bacteria Stick." in: *Scientific American*, vol. 238 No. 1, (Jan. 1978), pp. 86–95.

McCoy, W.F., Bryers, J.D., Robbins, J., Costerton, J.W., "Observations of Fouling Biofilm Formation." in: *1981 National Research Council of Canada*, (1981), pp. 910–917.

(List continued on next page.)

*Primary Examiner*—George Yeung
*Attorney, Agent, or Firm*—Welsh & Katz, Ltd.

[57] ABSTRACT

Apparatus for testing samples and specimens for microorganisms is provided. The apparatus comprises inoculating means for transferring an inoculum from one medium to another medium; positioning means for positioning the inoculating means in a predetermined position; container means for containing a fluid, semifluid, or solid medium, a sample, and the inoculating means; first aperture means for introducing a sample and a fluid, semi-fluid or solid medium into the container means; second aperture means for introducing the inoculating means into the container means; cap means for closing the second aperture means and for securing the positioning means so that the inoculating means is disposed in a predetermined position in the container means; and, closure means for closing the container means to separate the sample, the fluid medium, and the inoculating means from the outside environment. In another embodiment of this invention, a method is provided for detecting microorganisms in samples or specimens. The method comprises the following steps. First, a sample and an inoculating device is incubated in one or more fluid, semi-fluid or solid media for a pre-selected time at a pre-selected temperature. Second, the inoculating device is removed from the medium in which it has been incubated, and is then used to inoculate at least one other medium, which may be a fluid, semifluid, or solid medium. Next, the inoculated medium is incubated and then tested in accordance with the tests for the microorganism for which the sample or specimen is being tested.

32 Claims, 13 Drawing Sheets

OTHER PUBLICATIONS

Lovett, J., Hunt, J.M., Francis, D.W., Heisick, J., *Bacteriological Analytical Manual,* "Isolation of *Campylobacter* Species." 6th ed. Association of Official Analytical Chemists, (1984). chapter 10, pp. 10.01–10.08.

Lovett, J., Hitchins, A.D., *Bacteriological Analytical Manual,* "*Listeria* Isolation." (Revised 13 Oct. 1988) 6th ed. Association of Official Analytical Chemists, (1984). chapter 29, pp. 29.01–29.02.

Andrews, W.H. Poelma, P.L., Wilson, C.R., *Bacteriological Analytical Manual,* "Isolation and Identification of *Salmonella* Species." 6th ed. Association of Official Analytical Chemists, (1984). chapter 7, pp. 7.01–7.18.

Poelma et al., "Salmonella." *Compendium of Methods for the Microbiological Examination of Foods,* 2nd ed. American Public Health Association, chapter 26, pp. 286–326, (1984).

Costerton et al., "Bacterial Biofilm in Nature and Disease" *Annual Review Microbial* 1987, Annual Reviews Inc., (1987), pp. 436–464.

Venkateswaran, K., Takai, T., Navarro, I.M., Nakano, H., Hashimoto, H., Siebeling R.J. "Ecology of Vibrio cholerae Non–01 and Salmonella spp. and Role of Zooplankton in Their Seasonal Distribution in Fukuyama Coastal Waters, Japan." *Applied and Environmental Microbiology,* vol. 55, No. 6 (Jun. 1989), pp. 1591–1598.

"Salmonella." in: *Official Methods of Analysis,* (15th Edition 1990), Agricultural Chemicals; Contaminants; Drugs vol. 1, pp. 467–476.

Gahan, Cormac G.M., Collins, J.K., "Listeriosis: biology and implications for the food industry." in: *Trends in Food Science & Technology Apr.* 1991, (1991, Elsevier Science Publishers Ltd, (UK), pp. 89–93. 0924/91/502.00.

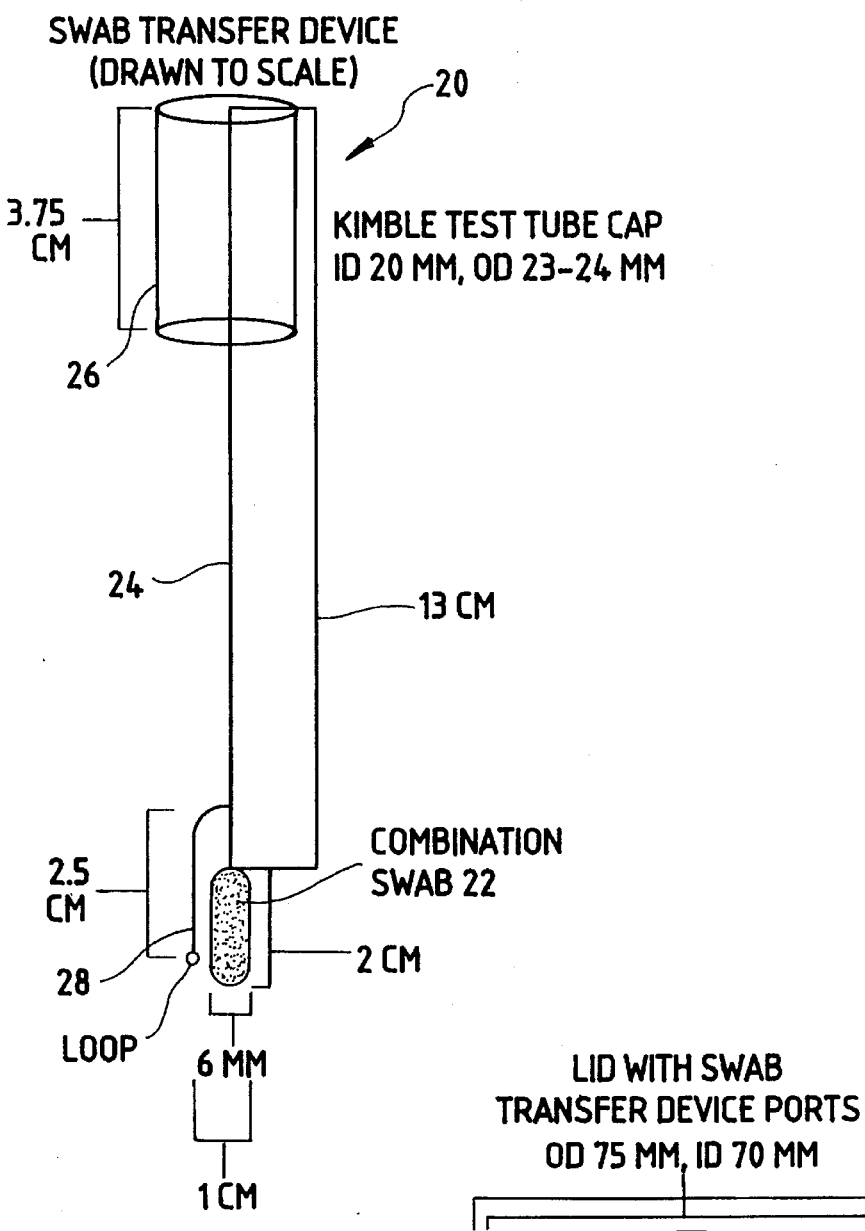
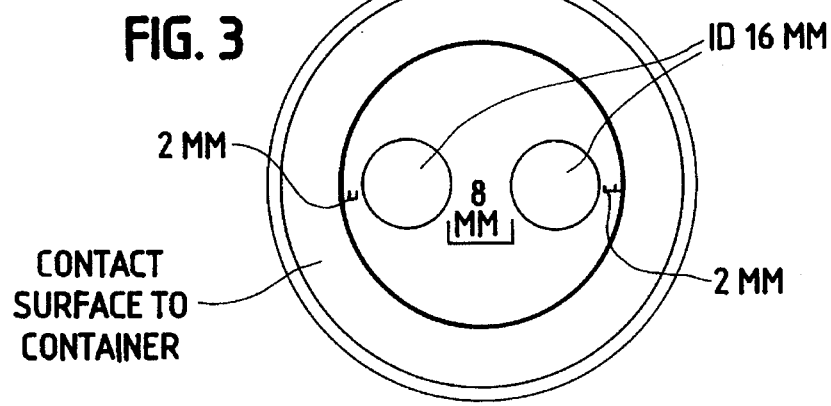

FIG. 5
EXTENDED SWAB IN LARGER CONTAINER
COMPRESSED SWAB IN TEST TUBE
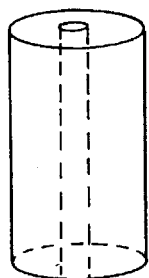
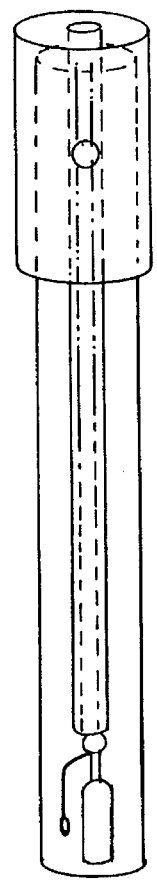
LEFT DIAGRAM
SWAB EXTENDED
TO REACH INTO
LARGE VOLUME
PRE-ENRICHMENT
RIGHT DIAGRAM
SWAB COMPRESSED
TO REACH FIT
INTO TEST TUBE
WITH SELECTIVE ENRICHMENT

PROPOSED SPONGE TRANSFER DEVICE

PROPOSED METHOD INCORPORATED A NOVEL SPONGE TRANSFER DEVICE FOR RECOVERY OF LISTERIA FROM ENVIRONMENTAL SAMPLES

CULTURE AND TRANSFER DEVICE FOR ENHANCED RECOVERY AND ISOLATION OF MICROORGANISMS

This application is a divisional of Ser. No. 07/990,572 filed on Dec. 14, 1992 entitled NOVEL CULTURE AND TRANSFER DEVICE FOR ENCHANCED RECOVERY AND ISOLATION OF MICROORGANISMS now abandoned.

BACKGROUND OF THE INVENTION

This invention relates to an improved method and apparatus for testing samples for the presence of microorganisms, such as Salmonella and Listeria, and Campylobacter.

Salmonella Bacterium.

Salmonella is a genus of bacteria responsible for a wide range of quite serious enteric infections often spread through food, water, and feeds. Salmonellosis usually is the primary bacterial cause of common foodborne diseases in North American and Europe according to national public health statistics. The disease can range from a self-limiting gastroenteritis with mild gastroenteric symptoms of diarrhea, fever, vomiting, and/or cramping to very severe, life-threatening gastroenteritis with or without bacteriemia. Although salmonellosis is generally considered a self-limiting illness, estimates of 9,000 deaths per year from approximately 2,000,000 cases annually have been reported for the United States. However, although the health statistics are useful in detecting trends or major outbreaks, the numbers reported are significant underestimates of actual cases. It is generally believed that only 1–10% of the cases are reported to public health authorities. Furthermore, due to changes in eating habits and international trade of ingredients and finished product, the incidence of salmonellosis in the United States and many other countries is on the increase. Cost estimates of almost $30,000 per case per outbreak resulting from investigated Salmonella outbreaks have been made. Thus, the detection of Salmonella, as well as other food-borne pathogens, in foods, feeds, and the environment is of great public health concern.

Listeria Bacterium.

Interest in the occurrence of Listeria and particularly Listeria monocytogenes in food and food-processing environments continues unabated as the result of four listeriosis outbreaks during the 1980's that were linked to coleslaw, pasteurized milk and two types of cheese—California-made, Jalisco-brand Mexican-style cheese and Swiss-made, Vacherin Mont d'Or soft-ripened cheese. Overall, these outbreaks resulted in over 500 cases of listeriosis and included at least 110 deaths.

In response to these outbreaks, the United States and many European countries began large-scale programs to determine the incidence of this pathogen in a wide variety of foods. As of 1990, a total of 76 Class I recalls were issued in the United States for Listeria contaminated dairy, meat and seafood products which resulted in staggering financial losses for the food industry. A similar situation is known to exist in Europe with the isolation of L. monocytogenes from all food types examined in the United Kingdom except baked beans and bottled water. Nonetheless, European recalls of Listeria-contaminated products have been relatively rare.

Present evidence indicates that Listeria enters most foods as a post-processing contaminant. Hence, the key to producing a Listeria-free product is to eliminate this organism from the food-processing environment. This is also the main principle on which the widely recognized Hazard Analysis Critical Control Point (HACCP) concept was founded over 20 years ago. Given this information, a clear need exists to optimize recovery of Listeria from the food-processing environment.

Present Methods Of Detecting Microorganisms Such As Salmonella And Listeria

Microorganisms found in foods and ingredients are often stressed as a result of food processing conditions. This applies to microorganisms that are human pathogens like Salmonella and Listeria, or other pathogens, as well as food spoilage microbes. Many of the processes used in manufacture of foodstuffs are designed to reduce or eliminate the microbiological population in or on the food to prevent illness in the consumer or to extend shelf-life of the product. Unless the process is sterilization, some cells survive processing. The cells which survive are usually injured and debilitated by processing and are consequently more difficult to isolate. Salmonella and Listeria are examples of microorganisms affected in such a manner.

The problem is how to detect and isolate the debilitated, stressed Salmonella or Listeria which, if present, are present only in very low numbers and in the presence of other competing microorganisms. Furthermore, the inherent variety and variability of foods, ingredients, and feeds and environments sampled can affect the incidence of isolation.

Several methods have been used to obtain samples of liquids and foods or samples of environments in which foods are processed or packaged for Salmonella and Listeria testing. Solid food samples have been obtained by cutting pieces from food to be tested. The pieces are then ground for purposes of the testing that is discussed below. Samples of milk or other liquids have been obtained by use of aseptic valves, syringes, pipettes, cups, or direct from containers. Environmental samples have been obtained by swabbing a surface with sponges or other absorbent materials, such as gauze.

In addition to food testing, water samples have been tested for Salmonella and other microorganisms. Water has been collected for such testing in containers, and also by absorbent materials such as tampons, as is discussed in Venkateswaran, Takai, Navarro, Nakano, Hashimoto, and Siebeling, *Ecology of Vibrio cholerae Non-01 and Salmonella* spp. and Role of Zooplankton in Their Seasonal Distribution in Fukuyama Coastal Waters, Japan, Applied and Environmental Microbiology, pp. 1591–1598 June 1989). That article noted that, better isolation of an allochthonous pathogen, viz., Salmonella spp., was noticed from the water samples when swabs were employed. Another paper discloses the use of a water sampling device consisting of a wire:gauze:wire sandwich. (Venkateswaran et al., 1989 *Applied and Environmental Microbiology* 556:1591–1598.) Although the article noted that there appeared to be better isolation of Salmonella from water samples if such swabs were employed, no information or data was given in the publication, and no attempt was made to explain that phenomena.

Current Methods of Salmonella Detection

The Bacteriological Analytical Manual, (BAM) published by the Food and Drug Administration (FDA), Ch. 10 (6th Ed. 1984) ISBN 0-935584-29-3), and the *Official Methods of Analysis*, published by the Association of Official Analytical Chemists, pp. 467–476 (15th Ed. 1990) (AOAC) describe the current methodology for detection, isolation, and identification of Salmonella from samples of the type discussed above. In general terms the five steps are: 1) Pre-enrichment, 2) Selective enrichment, 3) Selective plating, 4) Biochemical screening, and 5) Serotyping.

The first step, pre-enrichment, consists of introducing the sample into a non-selective, nutritious, fluid medium at a 1:10 sample:medium ratio to allow the debilitated, stressed Salmonella cells, if present, to recuperate to a stable physiological state. Depending on the product, this pre-enrichment medium can differ. However, if a highly contaminated product, such as a raw flesh product, is being analyzed, then the testing is initiated with the selective enrichments.

After incubation for 24 hours at 35° C., a 1 milliliter (mL) quantity of the pre-enrichment culture is transferred to selective enrichment. Selective enrichment uses two specifically designed liquid media known as tetrathionate broth and selenite cysteine broth, to allow continued proliferation of Salmonella while restricting the growth of most other competitor bacteria through use of selectively inhibitory reagents. After a second incubation of 24 hours at 35° C., the selective enrichments are streak plated onto three solid selective agar media. These media are known as xylose lysine desoxycholate (XLD), Hektoen enteric (HE), and bismuth sulphite (BS) agars. The selective plating media restrict growth of non-Salmonella microorganisms while allowing visual recognition of pure, discrete suspect-Salmonella colonies. The Salmonella-suspect colonies are picked for biochemical screening to eliminate other microorganisms with similar identification characteristics as Salmonella. The specific metabolic characteristics of most Salmonella allow a differentiation from other microorganisms and allows a tentative generic identification as Salmonella. Serotyping provides the species-specific identification of the tentatively identified Salmonella isolate.

The exact description of the conventional materials and procedures is described by the FDA in BAM, the AOAC, and the *Compendium of Methods for the Microbiological Examination of Foods*, pages 286–326 (2nd Ed., American Public Health Association 1984).

Current Methods of Listeria Detection

The present procedure for recovering Listeria from food-processing environments is based on the current USDA method (FIG. 6) with the sample collected on a sterile sponge. In this procedure, an ethylene oxide-sterilized cellulose sponge is removed from its protective package using surgical gloves and placed in a sterile Whirl-Pak bag. After rehydrating the dry sponge with 50 mL of neutralizing buffer, the wet sponge is removed from the bag using a surgical glove and the sample is collected by wiping the sponge over the desired surface i.e. floor, drain, pipe or a piece of equipment. The sponge is then returned to the same Whirl-Pak bag which is appropriately labeled and shipped to the laboratory by overnight delivery for analysis. Upon receipt of the sample, ca. 50 mL of UVM Broth a selective enrichment broth for Listeria is added to the bag containing the sponge. After squeezing the bag to incorporate the contents of the sponge in the broth, the sample is incubated at 30° C. for 24 h. Following incubation, 0.1 mL of the broth is pipetted into an appropriately labeled test tube containing 10 mL of Fraser Broth, a semi-selective differential enrichment broth that turns black in the presence of metabolically active Listeria spp. and a few other bacteria. After 24 and 48 h of incubation at 35° C., the Fraser Broth enrichment is streaked to appropriately labeled Petri plates containing Lithium Chloride-Phenylethanol-Moxalactam Agar (LPM) and Modified Oxford Agar (MOX), both agars of which will selectively differentiate Listeria from other bacteria. Following 24 and 48 h of incubation at 35° C., five well isolated Listeria-like colonies from each plate are streaked to Trypticase Soy Agar+Yeast Extract (TSAYE), a nutritious non-selective medium for re-isolation and purification of the suspected Listeria isolate. After 24 h of incubation at 35° C., each organism is examined for catalase activity. Gram-positive, catalase-positive, bacilli are then further characterized using the CAMP reaction, biochemical and serological reactions for identification of Listeria spp., including *L. monocytogenes*.

Current Methods Of Detection Of Other Microorganisms

The exact description of the conventional materials and procedures for testing other microorganisms is described by the FDA in BAM, the AOAC, and the *Compendium of Methods for the Microbiological Examination of Foods*, (2nd Ed., American Public Health Association 1984), and is known to those skilled in the art. Each of the methods of isolation involves the steps of transferring a sample into one or more enrichment media, and then transferring a sample from the enrichment medium into another medium for isolation. For example, the methods of detection of *E. coli* and other coliforms involves placing a food sample homogenate in an lauryl sulfate tryptose (LST) medium, incubating the sample in the broth, transferring a sample to a brilliant green lactose bile broth, and performing a biochemical analysis on positive samples thereafter. According to BAM, isolation of Shigella involves transferring a sample into a broth, incubating the broth, and then removing a portion of the incubated broth and inoculating MacConkey agar, and streaking it on the agar. Similar transfers are involved with the detection of other microorganisms, such as Campylobacter, Vibrio species, *Staphylococcus aureus*, *Bacillus cereus*, and *Clostridium botulinum*.

There are several drawbacks to the present methods for detection, isolation, and identification of microorganisms, such as Salmonella and Listeria. First, the methods currently used to isolate those and other microorganisms require separate steps of transferring samples. For example, in the case of Salmonella and Listeria, after the sample is initially incubated, a portion of it must be transferred to a pre-enrichment broth; and second, after further incubation, samples of selective enrichment must be streak plated onto agar media. The first transfer involves the use of a pipette or a syringe. The second transfer also involves the use of a separate device. In both cases, workers may be exposed to the bacteria and the sample may be subject to contamination. In addition, there is a danger of mislabeling samples. The same problems exist with the methods used to detect other microorganisms.

THE DRAWINGS

FIG. 2 is a schematic diagram of one embodiment of a swab transfer device which may be used in accordance with the present invention.

FIG. 3 is a schematic diagram of one embodiment of a lid for a container adapted to hold a swab transfer device in accordance with the present invention.

FIG. 5 is a schematic diagram of another embodiment of the present invention.

SUMMARY OF THE INVENTION

Figure 1:
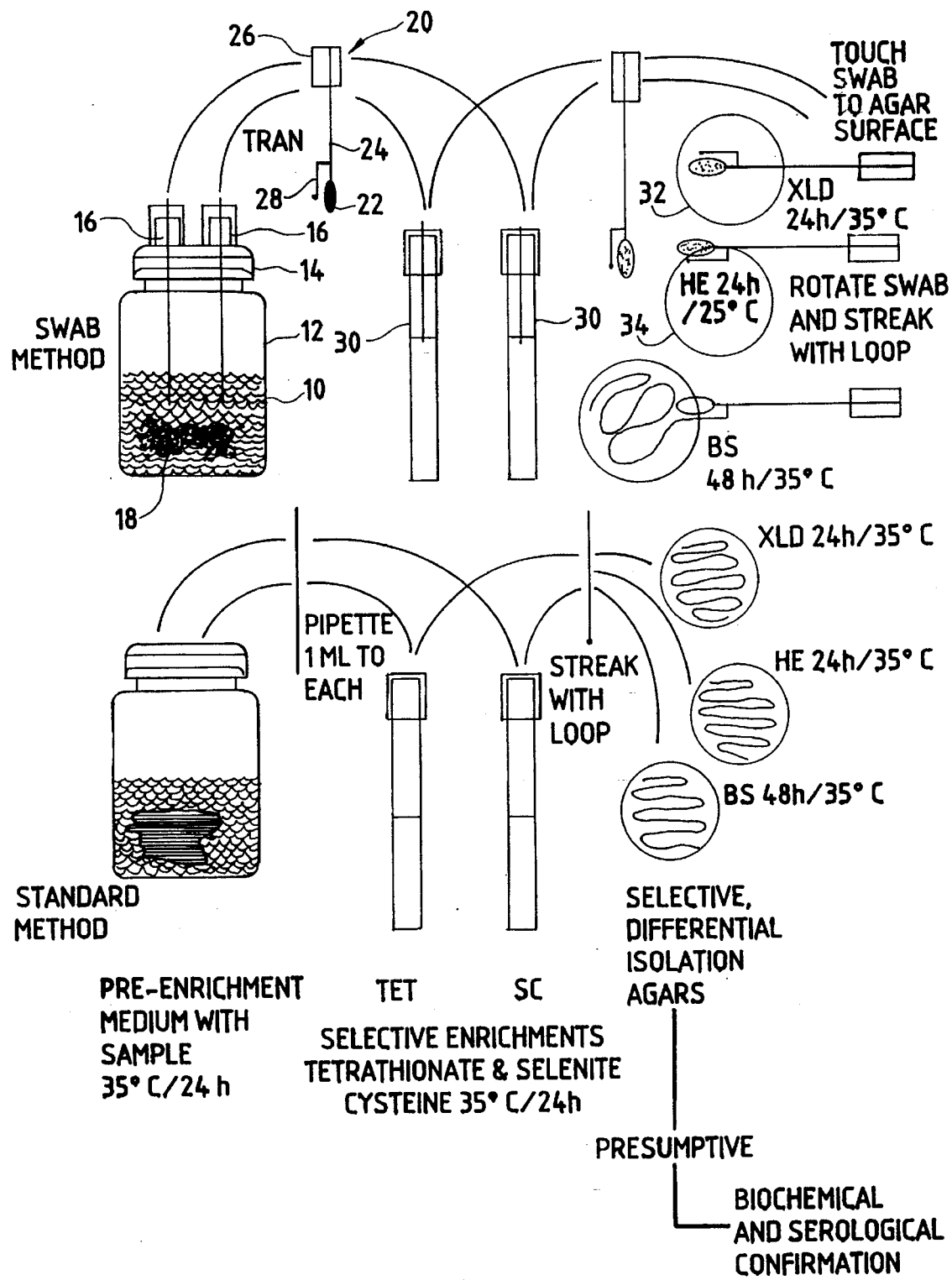
FIG. 1 is a schematic diagram comparing the apparatus and method of the present invention for detecting pathogens such as Salmonella in food samples with apparatus and method of the prior art.

The present invention provides an apparatus for detecting microorganisms in samples or specimens. The samples may include food samples, environmental samples, or other samples to which the method and apparatus are useful. The apparatus comprises inoculating means for transferring an inoculum from one medium to another medium; positioning means for positioning the inoculating means in a predetermined position; container means for containing a fluid, semifluid, or solid medium, a sample, and the inoculating means; first aperture means for introducing a sample and a fluid, semi-fluid or solid medium into the container means; second aperture means for introducing the inoculating means into the container means; cap means for closing the second aperture means and for securing the positioning means so that the inoculating means is disposed in a predetermined position in the container means; and, closure means for closing the container means to separate the sample, the fluid medium, and the inoculating means from the outside environment.

In a preferred embodiment, the inoculating means may be made of a composition selected from the group consisting of natural fibers, synthetic fibers, blends of natural or synthetic fibers, sponge, wood, metal or plastic. The positioning means comprises a shaft, which may be made of wood, plastic or metal. The positioning means may be adjustable in length so that it may be extended so that the inoculating means is in predetermined position in larger containers, and contracted to fit in a standard sized test tube.

The inoculating means is preferably disposed on the end of the positioning means, and in preferred embodiments, consists of material selected from the group consisting of natural fibers, such as cotton, synthetic fibers, blends of natural or synthetic fibers, such as cotton/rayon blends, or sponge. Alternatively, the inoculating means and positioning means may both consist of an elongated rod made of wood, metal or plastic, the end of the rod being used as the inoculating means. In a preferred embodiment, the cap means for closing the second aperture means may be adapted to bear a label to identify the sample being tested. The closure means preferably seal the contents of the container means from the outside environment to prevent unwanted environmental contaminants from entering into the container.

In another embodiment of this invention an inocluating device is provided for collecting and/or transferring an inoculum from one medium in a container to another medium. The inoculating device comprises inoculating means for transferring an inoculum from one medium to another medium, cap means for securing the inoculating means in a fixed position in relation to the container; and, positioning means for positioning the inoculating means in a predetermined position in the container. The inoculating means may be selected from the group consisting of natural or synthetic fibers or blends, sponge, wood, metal or plastic. In a preferred embodiment, the inoculating means is disposed on one end of a shaft and the cap means, which may bear a label, is on the opposite end of the shaft. The cap is preferably adapted to seal an aperture in a closure for the container. In preferred embodiments, the inoculating means may be a swab, such as a cotton swab, or a sponge. The swab may be made of material selected from the group consisting of cotton, cotton/synthetic blends, or sponge, or any other material suitable for the purpose for which the inoculating device is used. The shaft may comprise an elongated rod selected from the group consisting of wood, plastic, or metal. The shaft may be further provided with streaking means for streaking the sample onto plating media. The shaft may be adjustable so that the inoculating means may be extended to be placed in a predetermined position in a large container and contracted to fit in a test tube.

In one embodiment of this invention, an inoculating device, which is also used to collect environmental samples, may consist of a plastic shaft, which is provided on one end with a barrier, such as a cap, from which a portion of the shaft extends to act as a handle. The inoculating means consists of a sponge which is disposed on the other side of the barrier. The barrier isolates the handle of the shaft from the sponge, so that when the sponge is used to wipe an environmental surface to collect a sample, the inoculating device can be handled without touching the sponge. Preferably, a label is provided, either on the barrier or on the handle to identify the sample. In a preferred embodiment, this inoculating device may fit into a centrifuge tube, and the barrier forms a cap to the tube. In this manner, the inoculating device may be maintained in a sterile condition when it is taken to a site from which a sample is to be collected. It may be removed from the tube, used to wipe an environmental surface to collect a sample, replaced in the tube and closed to keep the inoculating device free from other contaminants while being transported to a testing lab.

In another embodiment of this invention, a method is provided for detecting microorganisms in samples or specimens. The method comprises the following steps. First, a sample and an inoculating device is incubated in one or more fluid, semifluid or solid media for a pre-selected time at a pre-selected temperature. Second, the inoculating device is removed from the medium in which it has been incubated, and is then used to inoculate at least one other medium, which may be a fluid, semifluid, or solid medium. Next, the inoculated medium is incubated and then tested in accordance with the tests for the microorganism for which the sample or specimen is being tested.

The type and number of media in which the inoculating device and sample are incubated depends on the microorganisms for which the sample is being tested. In the case of highly contaminated foods or samples tested for Salmonella, for example, the sample and inoculating device are first incubated in a fluid, selective enrichment environment. In the case of non-highly contaminated foods, however, the sample and inoculating device are incubated first in a liquid pre-enrichment fluid medium, and then the inoculating device is incubated in the selective enrichment fluid medium.

Similarly, the type of media which are inoculated by the inoculating device depends on the microorganisms for which the sample is being tested. For Salmonella, for example, after the inoculating device is incubated in the selective enrichment fluid medium, it may be removed from the selective enrichment fluid medium, and it may be used to streak solid media, which are preferably solid agar media, with the inoculating device to deposit an inoculum. The inoculum is then streaked across the surface of the solid media. Typically, the solid media is then incubated for a predetermined time at a predetermined temperature. Thereafter, colonies on the solid media which exhibit characteristics of the desired microorganism are selected for biochemical screening. In some cases, the selected colonies are serotyped to provide specific identification of the microorganism.

Alternatively, instead of using solid agar media, one or more fluid media may be used for rapid detection assays, such as enzyme-linked immunosorbent assays, DNA hybridization, and other assays known to those skilled in the art. In the case where such assays are used, the inoculating device may be used to inoculate the assay media immediately after the inoculating device has been incubated in a medium in the presence of the sample.

It is particularly effective to position the inoculating device in the medium in which it is incubated in a predetermined location, which is preferably in the bottom third of the medium.

In another embodiment, a method is provided for detecting microorganisms on an environmental surface. The method comprises the following steps. First, an environmental surface is contacted with an inoculating device to collect microorganisms on the surface. Second, the inoculating device is incubated in one or more fluid media. The type of media depends on the microorganism for which the sample is being tested. The inoculating device is incubated for a pre-selected time at a pre-selected temperature. Preferably, the inoculating device is placed in a predetermined position in the selective enrichment medium. Next, the inoculating device is removed from the medium in which it has been incubated, and it is used to inoculate another medium. The medium to be inoculated depends on the microorganism for which the sample is being tested. In the case of Listeria, for example, solid media, which are preferably one or more solid agar media, are inoculated with the inoculating device to deposit an inoculum, which is then streaked across the surface of the solid media. The solid media is then incubated for a predetermined time at a predetermined temperature. Colonies on the solid media are selected which exhibit characteristics of the microorganisms for biochemical screening. In a preferred embodiment of this method, the inoculating device is first inserted into a first container after the sample has been collected, and the first container is sealed from the outside environment to enable the container to be transported from the site where the environmental sample was obtained to a testing site without further surface contamination of the inoculating medium. Part of the inoculating device is then incubated in a pre-enrichment broth for a predetermined time at a predetermined temperature, and is subsequently incubated in a selective enrichment broth for a predetermined time at a predetermined temperature. This method has worked well for Listeria, and also may be used for other microorganisms.

There are a number of advantages to using the apparatus and methods of the present invention over the prior art. Those advantages are described in detail below. Briefly, however, the apparatus and method of the present invention provide more sensitive detection of microorganisms. The apparatus and method of the present invention are also easier to use, safer for workers, less likely to allow cross-contamination of the laboratory environment, and less likely to lead to laboratory error than the methods and apparatus presently employed.

DETAILED DESCRIPTION OF THE INVENTION

FIG. 1 is a schematic diagram which compares the standard method of detecting pathogens such as Salmonella in food samples with the method and apparatus of this invention.

As shown in FIG. 1, in the present invention, an appropriate fluid or liquid microbiological medium 10 is prepared, introduced into the container 12, lid 14 attached, and the two ports 16 capped. After sterilization of the medium and cooling to less than or equal to 35° C., the lid is removed, a sample 18 is placed into the container with the medium, the lid replaced, and the caps covering the ports exchanged for those with the inoculating device 20. The inoculating device, includes inoculating means 22, which may be selected from the group consisting of natural or synthetic fibers or blends such as cotton, cotton/rayon blends, sponge, gauze, wood, plastic, metal or any suitable natural or synthetic solid surface or matrix to which microorganisms or pathogens attach or associate. It also includes a shaft 24 which is adapted to suspend the inoculating means 22 in a predetermined position in the container. The inoculating device 20 also includes a cap 26, which is adapted to seal ports 16 of container 12.

After the inoculating device 20 has been inserted into container 12, the method of this invention is similar to the standard procedures of BAM/AOAC pathogen isolation methodologies.

For example, to detect Salmonella, the sample 18 is incubated in the container 12 with the inoculating device 20. After the appropriate incubation time, the inoculating device 20 can be transferred to test tubes 30 for further fluid selective enrichment incubations before inoculating solid agar media 32 and 34, or used to directly inoculate solid agar media. Solid media are inoculated by touching the inoculating device 20 to the surface of the media. In a preferred embodiment, inoculating device 20 is provided with a streaking device 28, which is preferably made of plastic, and which may also be made of wood, metal or other suitable material, and rotating the device to streak the inoculum across the surface of the medium. The solid media, which are preferably solid agar media, are incubated as required by standard methods or appropriate for the analysis or experiment.

Alternatively, after the inoculating device 20 is incubated in a fluid, semifluid, or solid medium with the sample, the inoculating device 20 may be used to inoculate another medium, which is then incubated, and the other medium may be assayed for the microorganism of interest. It may be assayed in any manner known to those skilled in the art, including the rapid assay methods. As used in this application, the term assay or assaying includes all such methods known to those skilled in the art which are used to detect microorganisms.

Figure 4:
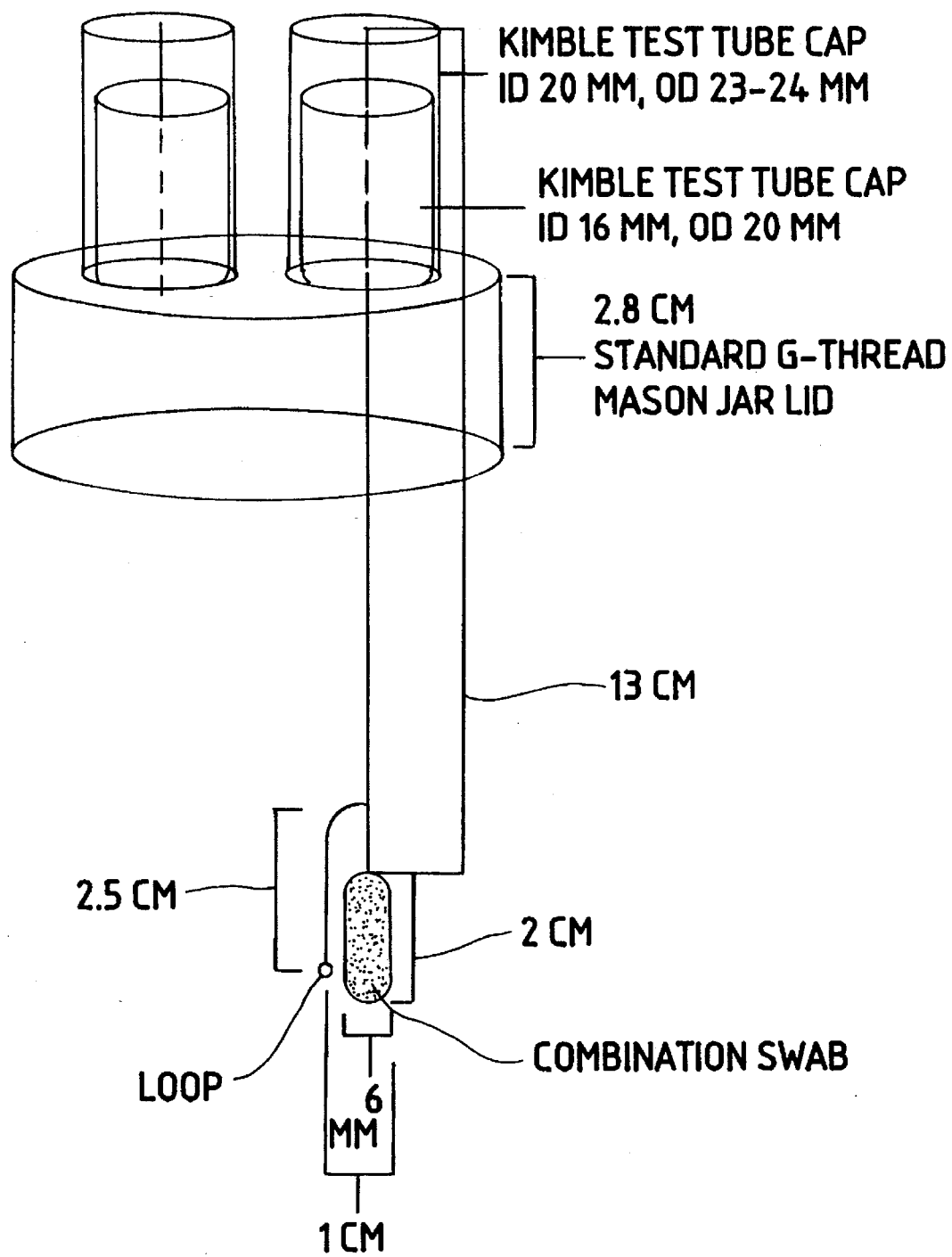
FIG. 4 is a schematic diagram of one embodiment of a swab transfer device and lid in accordance with the present invention.

FIGS. 2, 3 and 4 show one embodiment of the inoculating device 20 and cap 14 in accordance with the present invention. The inoculating device includes positioning means, which is preferably a shaft or rod 24. The length of the shaft and the other dimensions of the inoculating device can be adapted so that the inoculating device 20 may be used with current containers which may have a volume of up to 1 gal (US). It is optimal that the length of the shaft 24 be designed to suspend the inoculating means or swab in the lower portion of the container and to fit the length of standard sized test tubes. The dimensions shown in FIG. 2 were chosen to (1) conform with regularly used laboratory equipment such as standard threads on containers, (2) size the caps to fit test tubes, (3) adjust the swab length to fit test tube length, and (4) adjust the distance of loop arm from swab to fit through the port on the lid as well as fit into a test tube.

The means for inoculating the solid media shown in FIGS. 2, 4 and 5 may consist of a swab 22 located on the end of shaft 24. Swab 22 may consist of material selected from the group consisting of natural fibers, synthetic fibers, blends of natural and synthetic fibers, sponge, wood, metal or plastic. The shaft 24 comprises an elongated rod selected from the group consisting of wood, plastic, or metal. The shaft is further provided with streaking means for streaking the sample onto selective plating media.

FIG. 5 shows another embodiment of the invention in which shaft 24 is adapted to be extended to reach into a large volume pre-enrichment environment and to be compressed to fit into a standard sized test tube. In the embodiment shown, shaft 24 consists of two parts 30 and 32, which are in telescoping arrangement with one another. One end of the shaft 24 is secured to cap 34. Swab 22 is secured on the opposite end of the shaft. The shaft can be extended to position the swab 22 in a predetermined position in a large container, or it can be retracted so that the shaft and swab fit in a normal sized test tube.

A material of choice for the container and lid is polypropylene. Polypropylene possesses the proper heat-resistance characteristics allowing these pieces to be autoclaved. The cap device may also be of this material. Other suitable materials having similar properties may also be used. The active part of the device may be made of cast plastic and have an absorptive material, such as cotton, foam, cotton blends, sponge or the like, on the end. It may also be made of other materials, such as wood or metal. Parts may be cast, assembled, appropriately sterilized, and packaged. The materials discussed are by way of example only, and may be modified based on cost or performance characteristics of the substituted materials. At present, all materials used to construct the invention are commercially available. These parts are:

| Piece | Ordered From | Catalog # | Manufacturer | Part Number |
|---|---|---|---|---|
| Lid and container | Baxter | B7544-2 | Bel-Art | F109140000 |
| Inside port sleeve | Baxter | T1291-16 | Kimble | 7366016 |
| Outside port cap (end cap on swab) | Baxter | T1291-20 | Kimble | 7366020 |
| Swab, cotton | Baxter | A5000-2 | Hardwood Products | 258061W |
| Swab, Zero static | Baxter | A5012-7 | Wilshire Foam Products | HT1206 |
| Loops | Carlson Scientific | | CCP Scientific | 1401 |

The microbiological fluid media used for detection and isolation of Salmonella, Listeria, and Campylobacter with the invention are the standard media used for these purposes with the standard BAM/FDA, AOAC, USDA, and Compendium protocols, and are available from several commercial sources.

The cap of the inoculating device may bear a label, which will save labor since labeling is time-consuming and will help eliminate laboratory error as the label code will always physically be attached to the inoculating device. This will ensure that label and sample always correspond. Codes could be handwritten onto the surface of the cap, pasted with an adhesive label written by hand or from computer output, or a bar-code type label could be attached.

The caps on the access ports are of diameters such that they allow easy removal while providing a firm friction grip against one another. More importantly, there must be a 1–2 millimeter passageway on both sides between the exterior wall of the inside port sleeve and the interior wall of the cap on the inoculating device. This will allow gases generated by metabolizing microorganisms to be safely vented.

In a preferred embodiment of the invention, the swab 22 is positioned about 2.5 cm from the bottom of the pre-enrichment container and about 0.5 cm from the bottom of the test tubes containing the selective enrichment broths. The purpose in the first instance is to provide more intimate contact with the food sample, which although homogenized, tends to settle.

A statistical protocol of testing food and environmental samples was designed and initiated. The experiments used Salmonella as the model microbe but confirmation testing also involved Listeria and Campylobacter. Detection capabilities of the standard isolation methods were quantified and compared to the same methods incorporating the transfer device.

It appears that a foam-covered cotton swab is the preferred embodiment of the transfer device based on performance and cost.

Actual food and environmental samples were tested in a side-by-side comparison of the standard BAM/AOAC protocol and the swab technique incorporated into the BAM/AOAC protocol. The methodology was the standard methodology as proscribed in BAM as appropriate for the sample being analyzed. The only deviations from the standard protocol in the swab part of the methodology were 1) to add various swabs to the pre-enrichment broths, 2) to transfer swabs to individual selective enrichment broths as well as 1 mL as per BAM, and 3) to touch the swab to the isolation agar and then streak instead of using a 3 µL loop to sample and streak. All sample analyses began with one pre-enrichment being used as the starting point for both assays. In this manner the possibility of different sub-samples yielding different results was eliminated.

Several statistical procedures were used to draw performance comparisons correlating detection rate with volume, swab material, product, etc. Tests were performed both with and without equivalent data (i.e. all positive or all negative). Analysis of variance (ANOVA), paired t-tests, and linear regressions were performed on both standard and swab-modified methods. All tests were performed using a 0.05 level as the cut-off value for statistical significance. The ANOVA compared positive incidence as a function of methodology/swab material (BAM vs. different swabs), of product, and of volume.

As research progressed, superior performance was noted with certain swab materials. The less-promising swab materials and types were slowly eliminated from the testing protocol and replaced with others for evaluation. By statistical evaluation of performance, three swab types were chosen for complete evaluation. These were the cotton-tipped Cotton swab, a combination swab, and a zero static charge swab. The multiple experiments were needed to thoroughly evaluate the swab performance. Performance is summarized in the following tables.

TABLE 1

Comparison of performance of standard BAM methodology to swab modification of standard methodology

| Product | Total Tested | Number of samples detected | | | |
|---|---|---|---|---|---|
| | | BAM | Cotton | Combo | Zero |
| Batter | 50 | 6 | 8 | 7 | 10 |
| Meat and Bone Meal | 16 | 8 | 10 | — | — |
| Meat and Bone Meal | 23 | 14 | 15 | — | — |
| Meat and Bone Meal | 28 | 7 | 8 | — | — |
| Batter | 25 | 8 | 9 | — | — |
| NFDM | 10 | 1 | 1 | 1 | 1 |
| Pecans | 10 | 10 | 10 | 10 | 10 |
| Yeast | 10 | 0 | 0 | 0 | 0 |
| Cake Mix | 10 | 3 | 3 | 3 | 3 |
| Chicken Rinse Water | 10 | 10 | 10 | — | — |
| Environmental | 20 | 0 | 0 | 0 | 0 |
| Environmental | 6 | 2 | 2 | 4 | 2 |
| Meat and Bone Meal | 26 | 7 | 8 | — | 9 |
| Raw, Ground Pork | 30 | 22 | 24 | 26 | — |
| Cake Mix | 46 | 2 | 7 | 6 | 7 |
| Environmental | 37 | 4 | 6 | 7 | — |
| Spinach Powder | 25 | 5 | 6 | 7 | 6 |
| Batter | 50 | 3 | 5 | — | 6 |
| Milk Chocolate | 36 | 25 | — | 28 | 28 |
| Milk Chocolate | 36 | 22 | 26 | 25 | — |
| Total samples tested | | 504 | 468 | 326 | 299 |
| Samples Positive | | 159 | 158 | 124 | 82 |
| Detection relative to BAM/AOAC (%) | | 100.0 | 130.6 | 143.2 | 147.7 |

— not tested

TABLE 2

Comparison of performance of standard FDA and USDA methodology to swab modification of standard methodology for detection of Listeria monocytogenes

| Product | Total Tested | Number of samples detected | | | |
|---|---|---|---|---|---|
| | | FDA | Combo-FDA | USDA | Combo-USDA |
| Chinese foods/ingredients | 36 | — | — | 11 | 14 |
| Egg rolls | 6 | — | — | 2 | 3 |
| Cold-pack cheese | 50 | 0 | 0 | 0 | 0 |
| Crab (raw) | 32 | 0 | 0 | 0 | 0 |
| Gaucho beef | 50 | 14 | 22 | 37 | 38 |
| Chicken (raw) | 50 | 18 | 20 | 18 | 20 |
| Total samples tested | | 182 | 182 | 224 | 224 |
| Samples positive | | 32 | 42 | 68 | 75 |
| Detection relative to FDA or USDA | | 100.0 | 131.3 | 100.0 | 110.3 |

— not tested

TABLE 3

Comparison of performance of standard BAM methodology to swab modification of standard methodology for detection of Camplyobacter

| Product | Total Tested | Number Of Samples Detected | |
|---|---|---|---|
| | | BAM | Combo |
| Beef Skin | 32 | 0 | 0 |
| Beef Skin | 32 | 2 | 2 |
| Total Samples Tested | | 64 | 64 |
| Samples Positive | | 2 | 2 |
| Detection relative to BAM/AOAC (%) | | 100.0 | 100.0 |

Several conclusions can be drawn from these experiments. First, and most important, is the superiority of the swab performance. Statistical results/output are shown in Examples 1–6 and FIGS. 9–14. Performance was always equivalent or better than the standard method by roughly 30–48 percent with the Salmonella assay and 10–31 percent with Listeria. All samples which tested positive by the standard methods also tested positive using the apparatus and method of this invention. The converse, however, was not true. Superior performance of the present invention is very strongly supported by statistical analysis. The probability that the results were due to chance was less than one in ten thousand. The linear regression analysis comparing performance indicated the performance of standard versus swab methods were different at a 95% confidence interval (CI) with an $r^2$ of >0.95, as shown in Examples 1–6 and FIGS. 9–14. This means that the swab transfer device performance is consistently different and superior to the standard method. If zero points are deleted on the basis of no detection or if equivalent data are eliminated from the data sets, the results indicated an even greater swab performance difference. The elimination of these data can be justified as the question arises whether the all positive and all negative data demonstrate anything of statistical significance. If all results were positive, then perhaps differences in system performance were overwhelmed with high numbers of Salmonella, and if all results for both methods were negative, perhaps there was no difference in performance due to no viable Salmonella being present in the sample.

Other statistical analyses using the same cut-off criteria of 0.05 indicated that performance was not a matter of volume transferred as different size swabs and volumes were transferred and no statistically significant correlation was observed. In addition the analysis indicated that the material of the swab had an effect on recovery as different swabs detected Salmonella at different rates. The statistical analysis also indicated that performance was not limited to Salmonella. Recovery was enhanced for both Salmonella, a Gram-negative bacterium, and Listeria, a Gram-positive bacterium.

The foregoing results demonstrate that the claimed invention exhibits superior performance when compared to the standard apparatus and methods for isolation of microorganisms, such as Salmonella and Listeria or Campylobacter from food and environmental samples. The apparatus and method of the present invention are also useful for testing other microorganisms, such as other bacteria, yeasts, or molds.

One advantage of this invention is that worker safety is improved. The apparatus and method of this invention eliminate pipetting, which could result in infection or if mouth pipetting were used, it would eliminate potential for ingestion of microorganisms. Since pipettes are not used, workers are not exposed to cuts as the result of breakage of pipettes. Further, it reduces exposure to sanitation chemicals to eliminate contamination if pipettes drip or skin comes in contact with the media containing the sample. Some of these chemicals can cause chronic skin complaints. Indirectly, it reduces worker risk by reducing potential for environmental contamination of the laboratory.

Another advantage of the apparatus and method of this invention is increased convenience, increased ease of use, and increased efficiency in use. A further advantage of the apparatus and method of this invention is that it can potentially reduce laboratory error and save time through directly labeling the cap of the swab transfer device. Time savings will accrue by saving labor from labeling and error tracking. Statistical results of experiments are shown in the following Examples 1–6 and in FIGS. 9–14:

EXAMPLE 1

BAM/AOAC versus Cotton Swab Inoculation Device
Simple Regression $X_1$: # BAM positive $Y_1$: # cottom Q-tip positive

| DF: | R: | R-squared: | Adj. R-squared: | Std. Error: |
|---|---|---|---|---|
| 19 | .982 | .965 | .963 | 1.324 |

| Analysis of Variance Table | | | | |
|---|---|---|---|---|
| Source: | DF: | Sum Squares: | Mean Square: | F-test: |
| REGRESSION | 1 | 869.652 | 869.652 | 496.192 |
| RESIDUAL | 18 | 31.548 | 1.753 | p = .0001 |
| TOTAL | 19 | 901.2 | | |

No Residual Statistics Computed
  Note: 1 case deleted with missing values.
  Simple Regression $X_1$: # BAM positive $Y_1$: # cotton Q-tip positive

| Beta Coefficient Table | | | | | |
|---|---|---|---|---|---|
| Parameter: | Value: | Std. Eff.: | Std. Value: | t-Value: | Probability: |
| INTERCEPT | .731 | | | | |
| SLOPE | 1.075 | .048 | .982 | 22.275 | .0001 |

| Confidence Intervals Table | | | | |
|---|---|---|---|---|
| Parameter: | 95% Lower: | 95% Upper: | 90% Lower: | 90% Upper: |
| MEAN (X,Y) | 7.578 | 8.822 | 7.687 | 8.713 |
| SLOPE | .973 | 1.176 | .991 | 1.158 |

EXAMPLE 2

BAM/AOAC versus Cotton Swab Inoculation Device
Simple Regression $X_1$: # BAM positive $Y_1$: # combo positive

| DF: | R: | R-squared: | Adj. R-squared: | Std. Error: |
|---|---|---|---|---|
| 13 | .99 | .979 | .978 | 1.443 |

| Analysis of Variance Table | | | | |
|---|---|---|---|---|
| Source: | DF: | Sum Squares: | Mean Square: | F-test: |
| REGRESSION | 1 | 1186.456 | 1186.456 | 570.118 |
| RESIDUAL | 12 | 24.973 | 2.081 | p = .0001 |
| TOTAL | 13 | 1211.429 | | |

No Residual Statistics Computed
  Note: 7 case deleted with missing values.

Simple Regression $X_1$: # BAM positive $Y_1$: # combo positive

| Beta Coefficient Table | | | | | |
|---|---|---|---|---|---|
| Parameter: | Value: | Std. Eff.: | Std. Value: | t-Value: | Probability: |
| INTERCEPT | .922 | | | | |
| SLOPE | 1.091 | .046 | .99 | 23.877 | .0001 |

| Confidence Intervals Table | | | | |
|---|---|---|---|---|
| Parameter: | 95% Lower: | 95% Upper: | 90% Lower: | 90% Upper: |
| MEAN (X,Y) | 8.731 | 10.412 | 8.884 | 10.259 |
| SLOPE | .991 | 1.19 | 1.009 | 1.172 |

EXAMPLE 3

BAM/AOAC versus Cotton Swab Inoculation Device(zero points deleted)
Simple Regression $X_1$: # BAM positive $Y_1$: # cotton Q-tip positive

| DF: | R: | R-squared: | Adj. R-squared: | Std. Error: |
|---|---|---|---|---|
| 17 | .98 | .96 | .957 | 1.373 |

| Analysis of Variance Table | | | | |
|---|---|---|---|---|
| Source: | DF: | Sum Squares: | Mean Square: | F-test: |
| REGRESSION | 1 | 721.614 | 721.614 | 382.773 |
| RESIDUAL | 16 | 30.164 | 1.885 | p = .0001 |
| TOTAL | 13 | 751.778 | | |

No Residual Statistics Computed
  Note: 1 case deleted with missing values.
  Simple Regression $X_1$: # BAM positive $Y_1$: # cotton Q-tip positive

| Beta Coefficient Table | | | | | |
|---|---|---|---|---|---|
| Parameter: | Value: | Std. Eff.: | Std. Value: | t-Value: | Probability: |
| INTERCEPT | .947 | | | | |
| SLOPE | 1.057 | .054 | .98 | 19.565 | .0001 |

| Confidence Intervals Table | | | | |
|---|---|---|---|---|
| Parameter: | 95% Lower: | 95% Upper: | 90% Lower: | 90% Upper: |
| MEAN (X,Y) | 8.425 | 9.797 | 8.546 | 9.676 |
| SLOPE | .943 | 1.172 | .963 | 1.152 |

EXAMPLE 4

BAM/AOAC versus Cotton Swab Inocluation Device(zero points deleted)

Simple Regression $X_1$: # BAM positive $Y_1$: # combo positive

| DF: | R: | R-squared: | Adj. R-squared: | Std. Error: |
|---|---|---|---|---|
| 11 | .989 | .977 | .975 | 1.505 |

Analysis of Variance Table

| Source: | DF: | Sum Squares: | Mean Square: | F-test: |
|---|---|---|---|---|
| REGRESSION | 1 | 975.019 | 975.019 | 430.524 |
| RESIDUAL | 10 | 22.647 | 2.265 | p = .0001 |
| TOTAL | 11 | 997.667 | | |

No Residual Statistics Computed

Note: 7 case deleted with missing values.

Simple Regression $X_1$: # BAM positive $Y_1$: # cotton Q-tip positive

Beta Coefficient Table

| Parameter: | Value: | Std. Eff.: | Std. Value: | t-Value: | Probability: |
|---|---|---|---|---|---|
| INTERCEPT | 1.261 | | | | |
| SLOPE | 1.071 | .052 | .989 | 20.749 | .0001 |

Confidence Intervals Table

| Parameter: | 95% Lower: | 95% Upper: | 90% Lower: | 90% Upper: |
|---|---|---|---|---|
| MEAN (X, Y) | 10.199 | 12.135 | 10.379 | 11.954 |
| SLOPE | .956 | 1.186 | .977 | 1.164 |

EXAMPLE 5

BAM/AOAC versus Cotton Swab Inoculation Device. (equivalent data deleted)

Simple Regression $X_1$: # BAM positive $Y_1$: # cottom Q-tip positive

| DF: | R: | R-squared: | Adj. R-squared: | Std. Error: |
|---|---|---|---|---|
| 13 | .983 | .967 | .964 | 1.332 |

Analysis of Variance Table

| Source: | DF: | Sum Squares: | Mean Square: | F-test: |
|---|---|---|---|---|
| REGRESSION | 1 | 614.719 | 614.719 | 346.628 |
| RESIDUAL | 12 | 21.281 | 1.773 | p = .0001 |
| TOTAL | 13 | 636 | | |

No Residual Statistics Computed

Note: 1 case deleted with missing values.

Simple Regression $X_1$: # BAM positive $Y_1$: # cotton Q-tip positive

Beta Coefficient Table

| Parameter: | Value: | Std. Eff.: | Std. Value: | t-Value: | Probability: |
|---|---|---|---|---|---|
| INTERCEPT | 1.427 | | | | |
| SLOPE | 1.044 | .056 | .983 | 18.618 | .0001 |

Confidence Intervals Table

| Parameter: | 95% Lower: | 95% Upper: | 90% Lower: | 90% Upper: |
|---|---|---|---|---|
| MEAN (X, Y) | 9.224 | 10.776 | 9.366 | 10.634 |
| SLOPE | .922 | 1.166 | .944 | 1.144 |

EXAMPLE 6

BAM/AOAC versus Cotton Swab Inoculation Device. (equivalent data deleted)

Simple Regression $X_1$: # BAM positive $Y_1$: # combo positive

| DF: | R: | R-squared: | Adj. R-squared: | Std. Error: |
|---|---|---|---|---|
| 7 | .997 | .995 | .994 | 832 |

Analysis of Variance Table

| Source: | DF: | Sum Squares: | Mean Square: | F-test: |
|---|---|---|---|---|
| REGRESSION | 1 | 767.351 | 767.351 | 1109.657 |
| RESIDUAL | 6 | 4.149 | .692 | p = .0001 |
| TOTAL | 7 | 771.5 | | |

No Residual Statistics Computed

Note: 7 case deleted with missing values.

Simple Regression $X_1$: # BAM positive $Y_1$: # combo positive

Beta Coefficient Table

| Parameter: | Value: | Std. Eff.: | Std. Value: | t-Value: | Probability: |
|---|---|---|---|---|---|
| INTERCEPT | 2.53 | | | | |
| SLOPE | 1.032 | .031 | .997 | 33.312 | .0001 |

Confidence Intervals Table

| Parameter: | 95% Lower: | 95% Upper: | 90% Lower: | 90% Upper: |
|---|---|---|---|---|
| MEAN (X, Y) | 13.03 | 14.47 | 13.179 | 14.321 |
| SLOPE | .956 | 1.108 | .972 | 1.092 |

Figure 6:
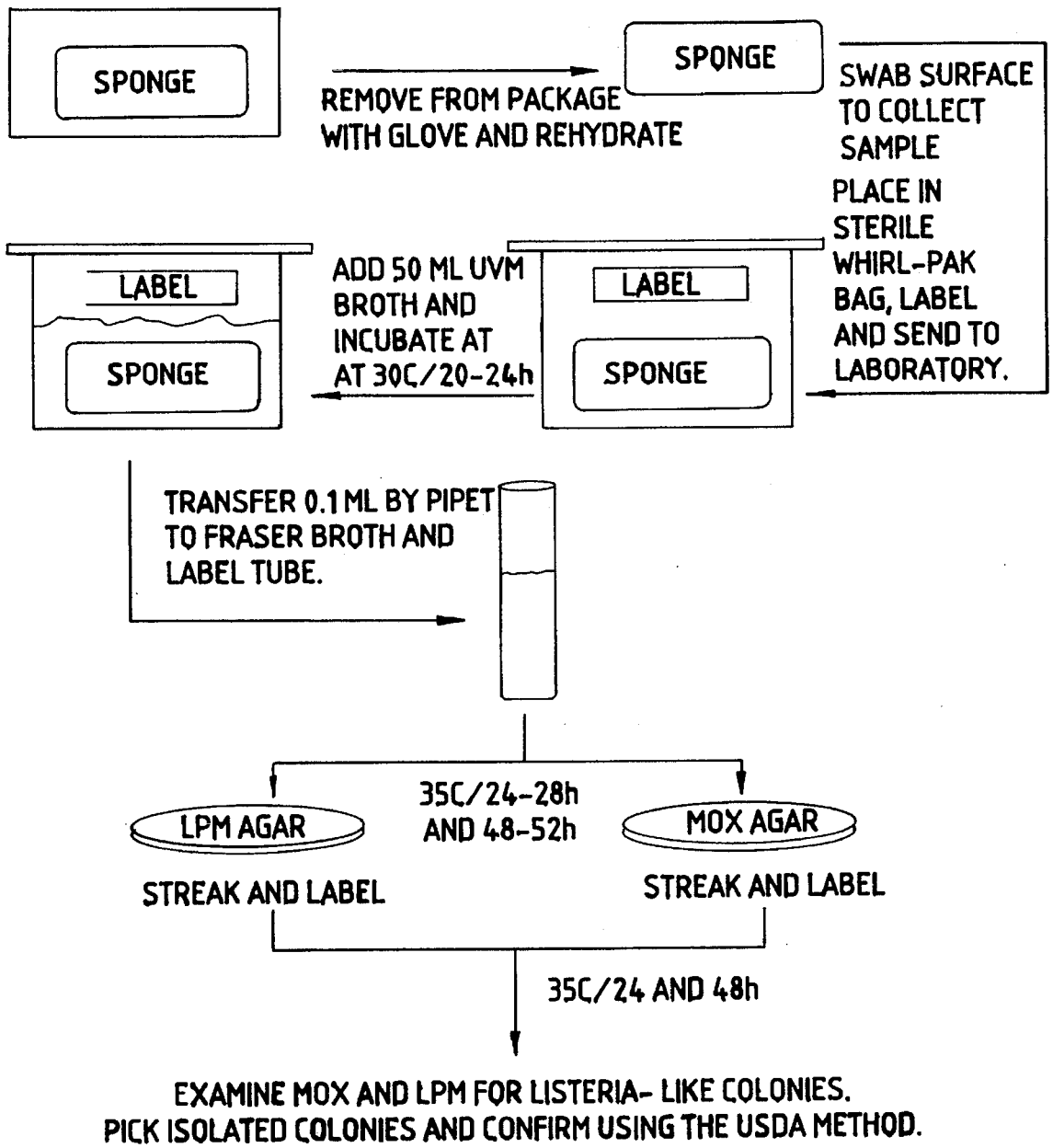
FIG. 6 is a schematic flow diagram illustrating the present method of recovering pathogens such as Listeria from environmental samples.

Another embodiment of this invention provides for an improved apparatus and a method for recovery of Listeria spp. from food-processing environments. FIG. 6 is a flow chart that illustrates the current USDA method for recovery of Listeria from environmental samples.

Figure 7:
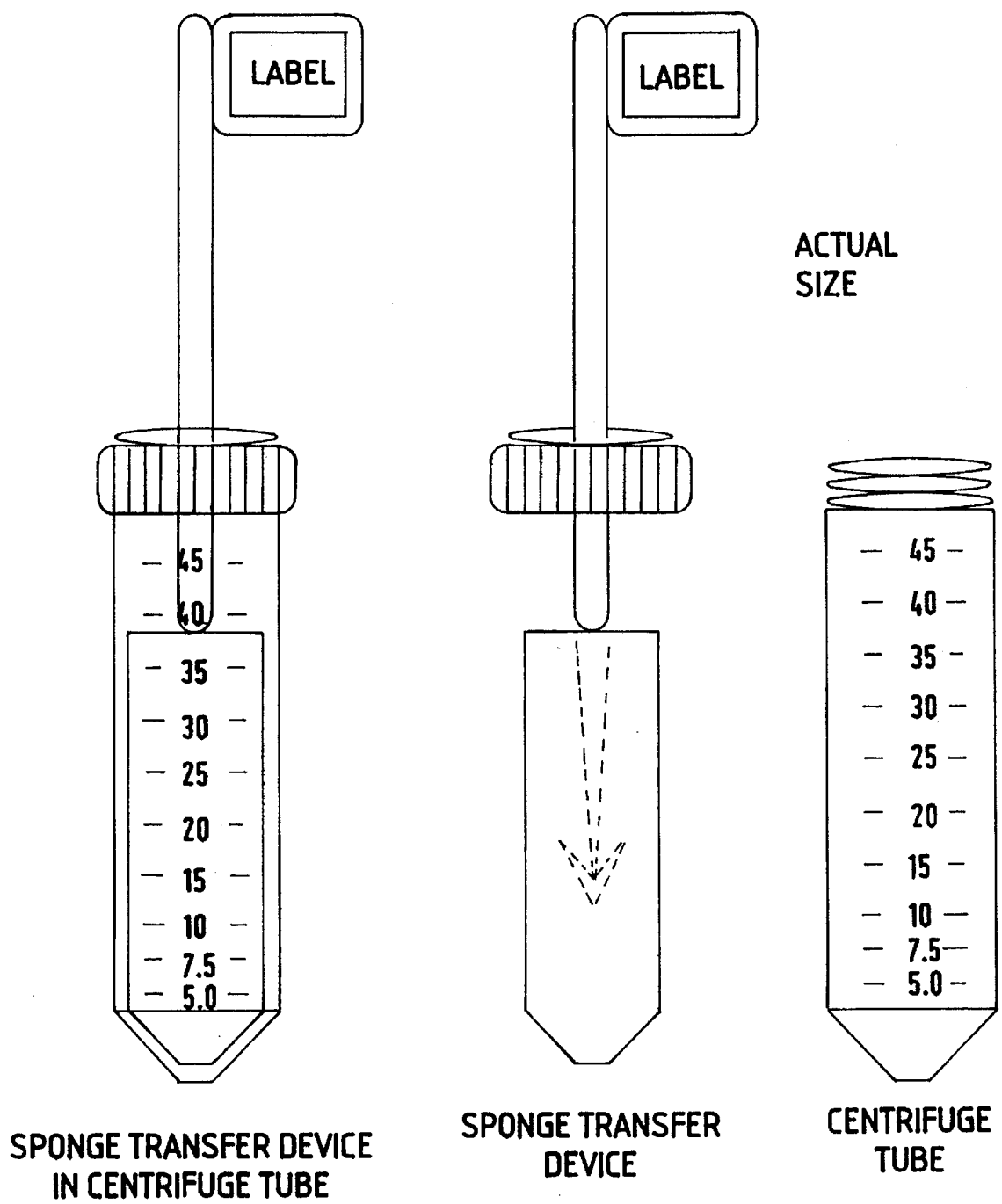
FIG. 7 is a schematic diagram illustrating one embodiment of the present invention for recovering pathogens such as Listeria from environmental samples.

FIG. 7 shows a preferred embodiment of an apparatus in accordance with the present invention. The apparatus includes two major components:

1. The currently used ethylene oxide-sterilized cellulose sponge which has been fashioned into a cylinder with a cone-shaped bottom and attached to a sturdy plastic stick with an attached screw cap and an area for a label.
2. An ethylene oxide-sterilized disposable, graduated, conical 50 mL screw cap centrifuge tube composed of polypropylene or polyethylene (similar to VWR 21008-124) to hold the aforementioned sponge device.

The two components fit together so that the sterile sponge device is contained within the sterile centrifuge tube.

Figure 8:
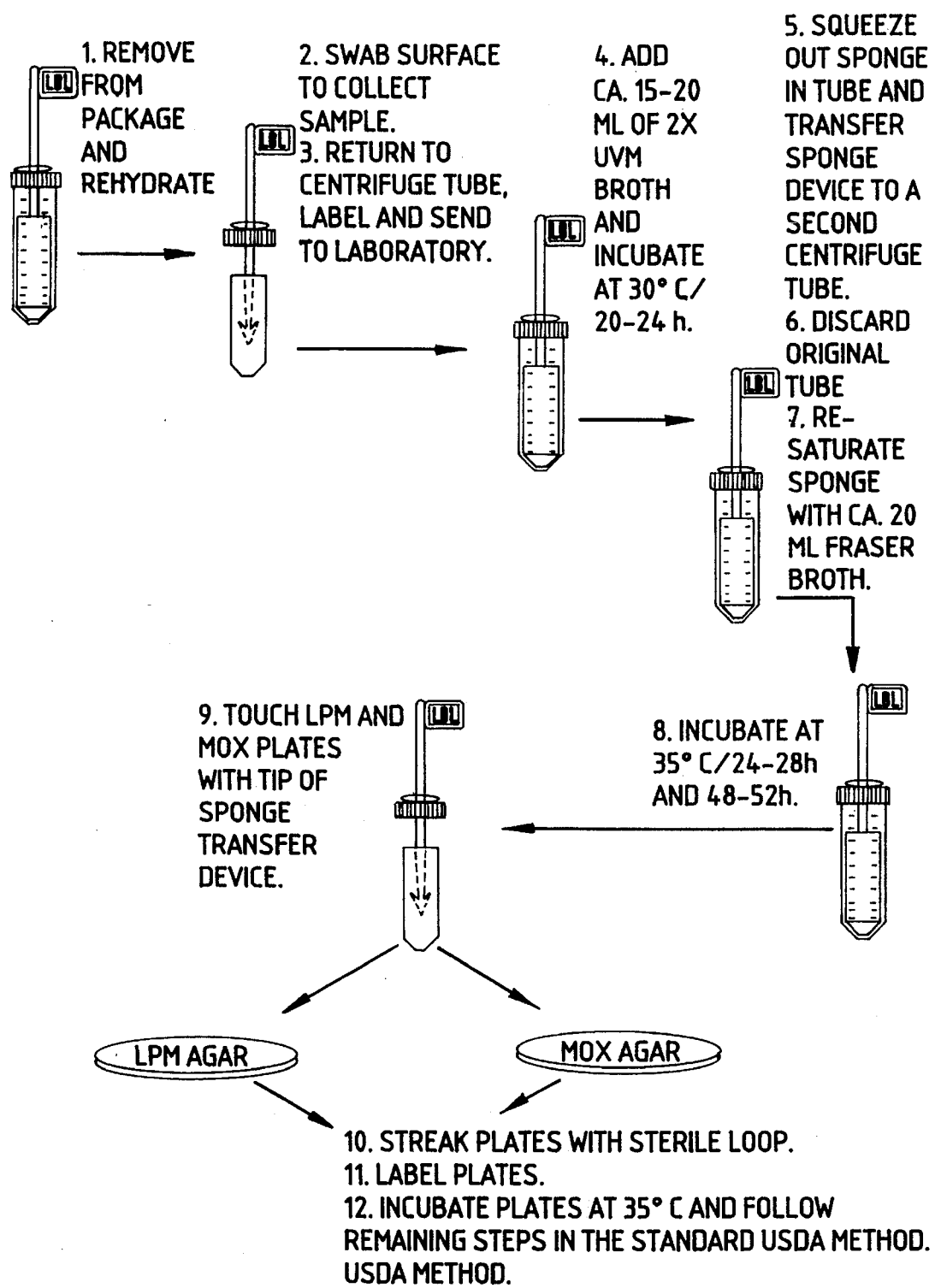
FIG. 8 is a schematic diagram illustrating a method of the present invention for recovering pathogens such as Listeria from environmental samples.
Figure 9:
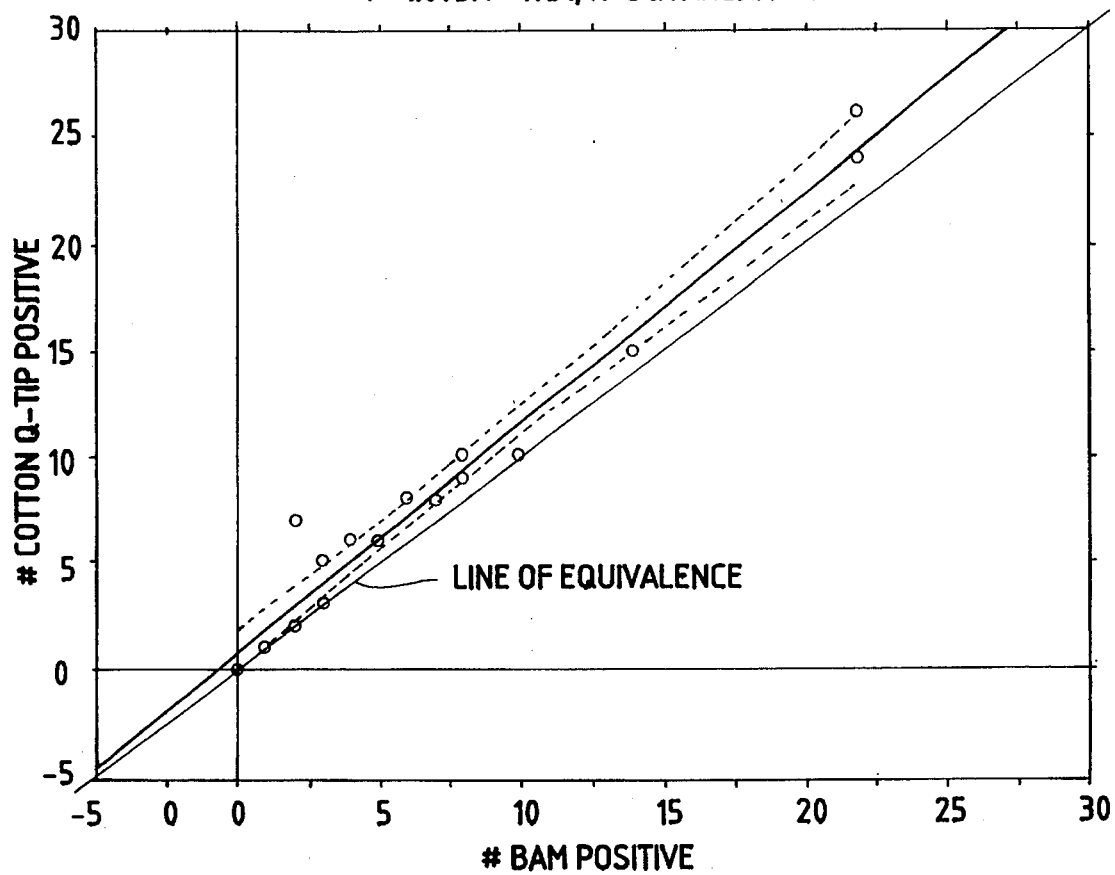
FIGS. 9–14 are graphs showing date from Examples 1–6.
Figure 10:
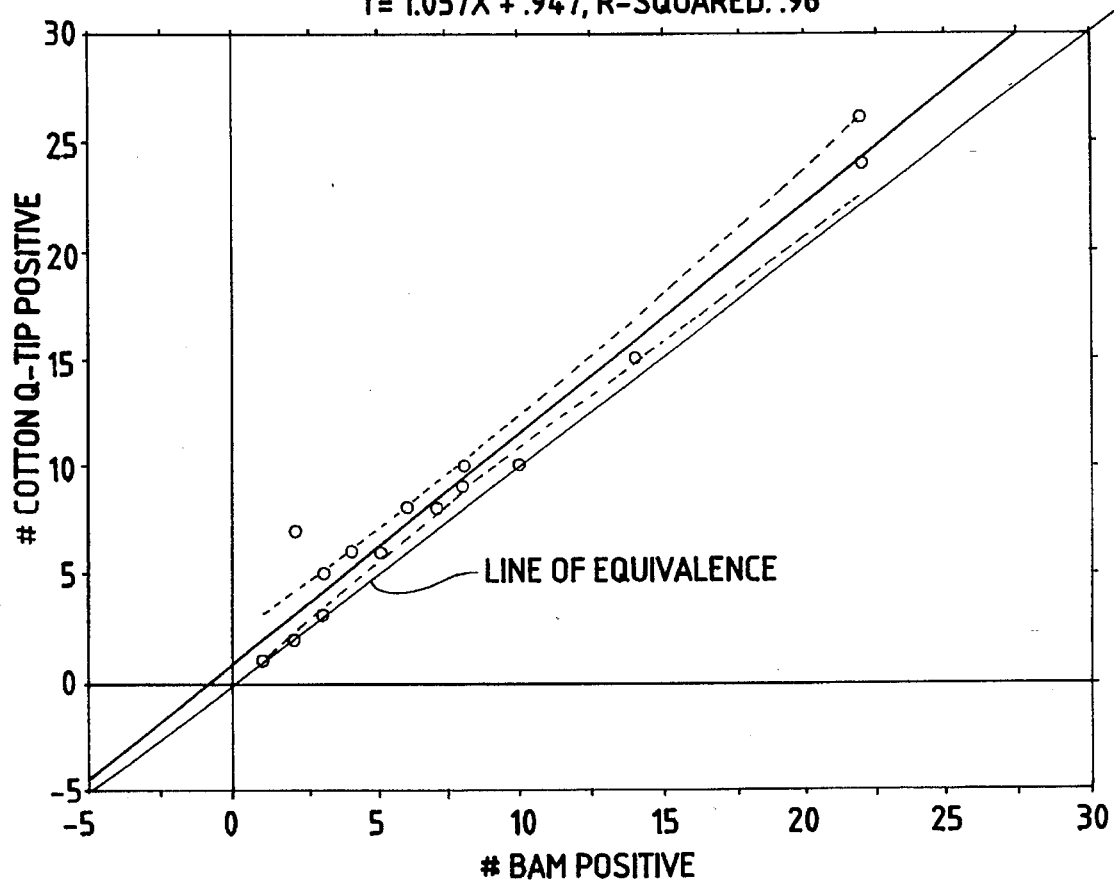
Figure 11:
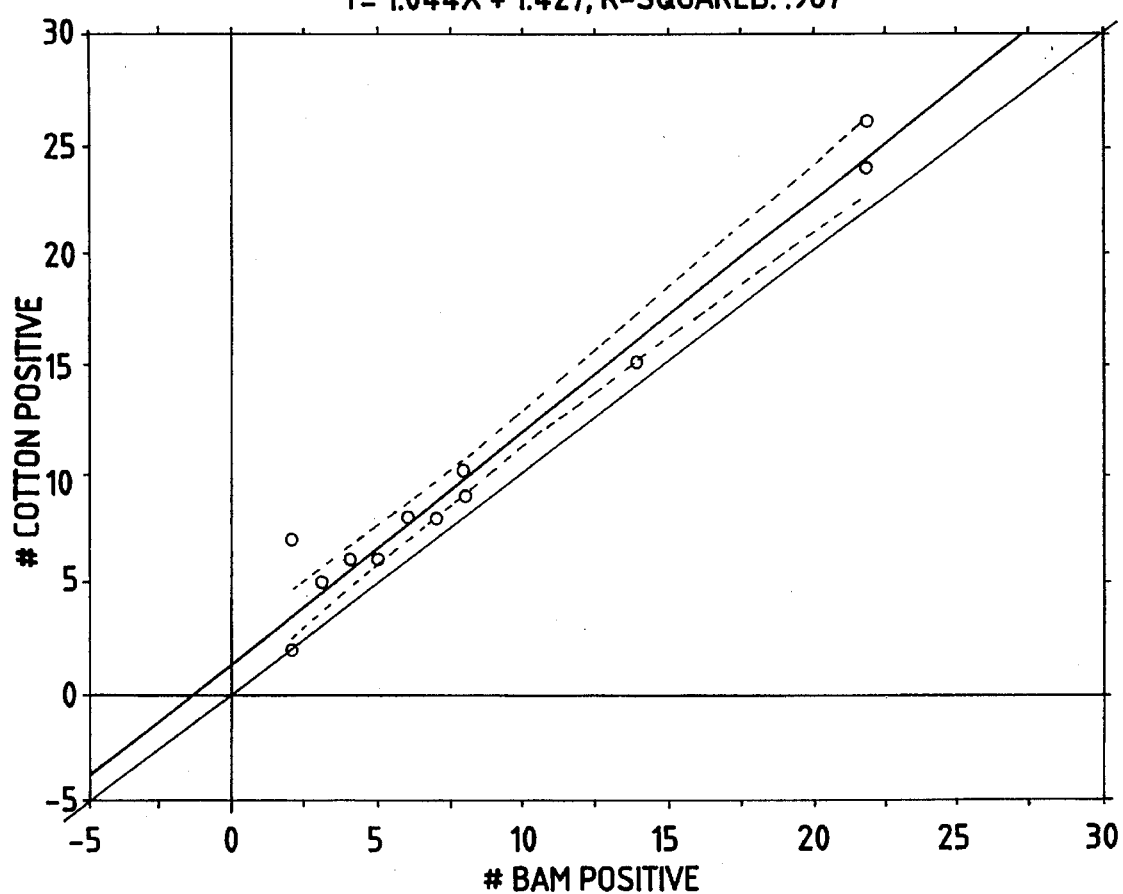
Figure 12:
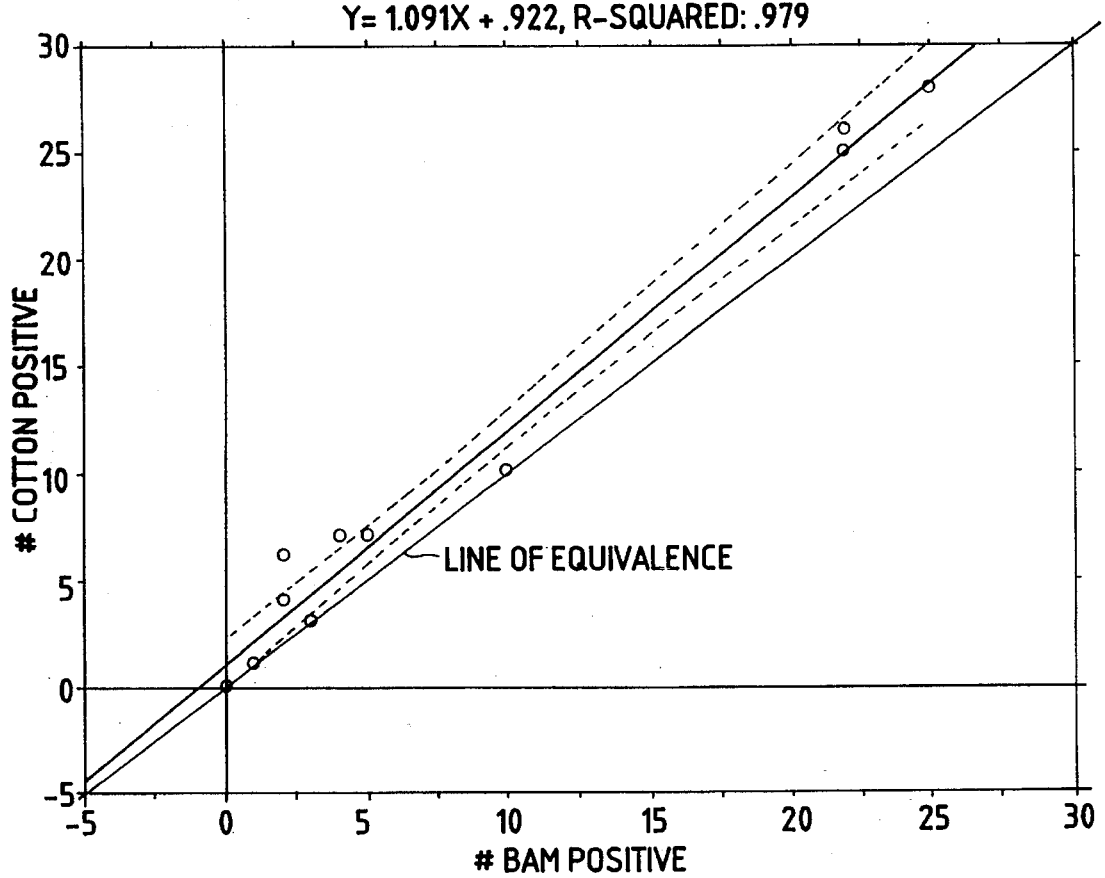
Figure 13:
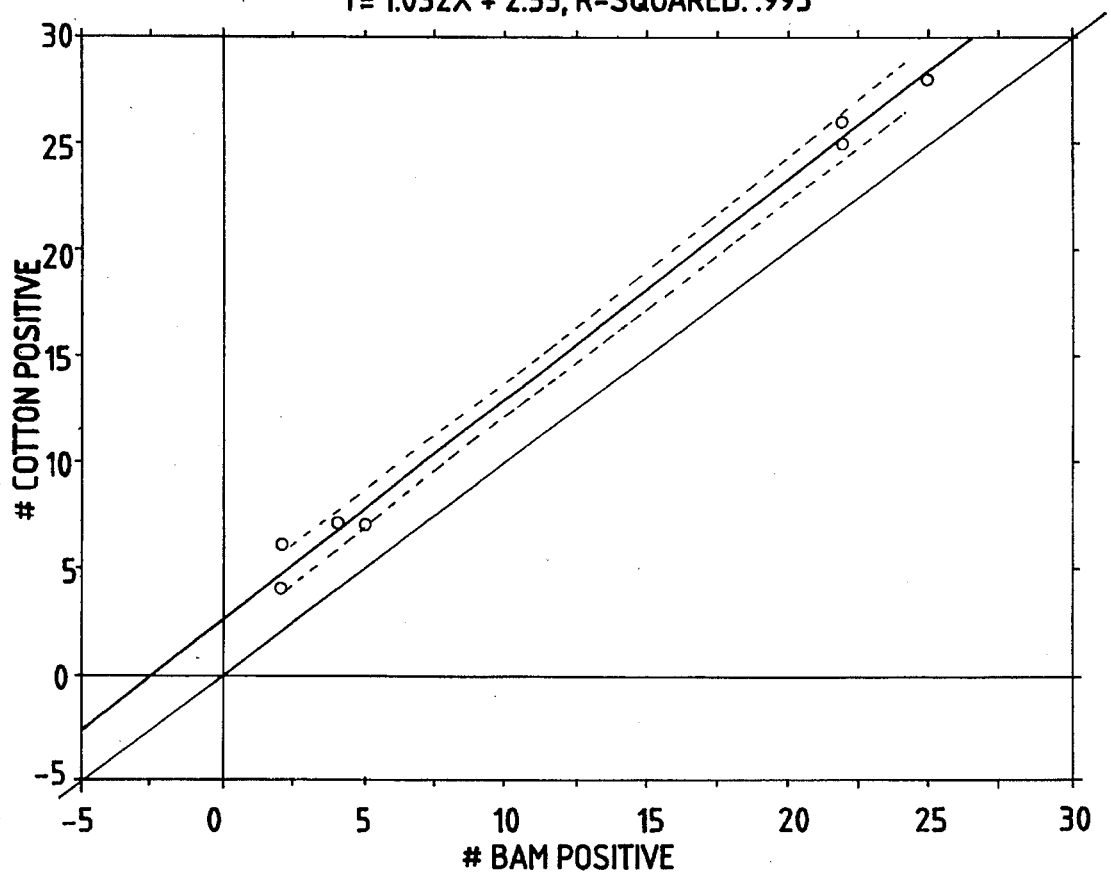
Figure 14:
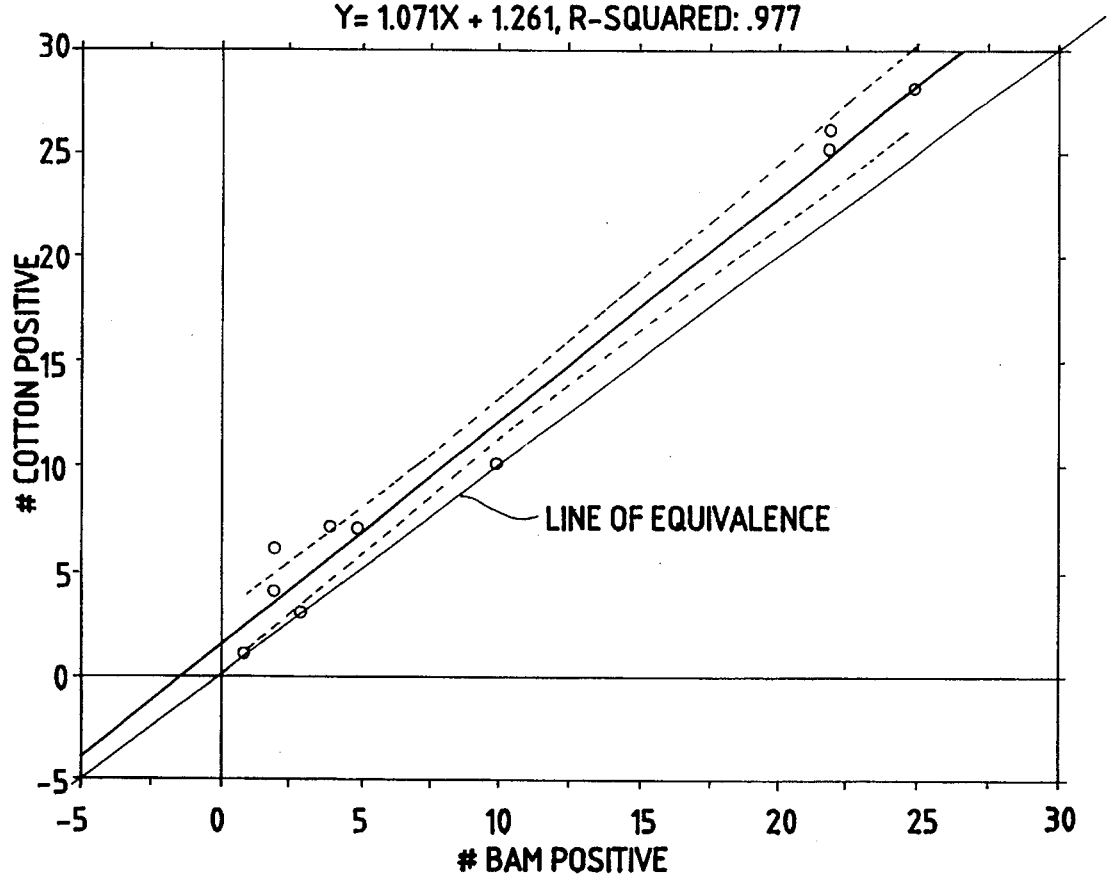

This invention also includes an improved method for recovering Listeria spp. from food-processing environments. That method utilizes the same media used in the USDA procedure; however, handling of the sample is markedly different, as shown in FIG. 8. In the proposed method, the cap of the centrifuge tube is unscrewed to remove the sponge device. Holding the device with bare hands behind the cap, the sponge portion is inserted into a container of sterile neutralizing buffer for rehydration and then gently pressed against the side of the container to remove excess liquid. The rehydrated sponge is then swabbed over the surface to be tested with the conical end of the sponge specially adapted to reach areas that are difficult to sample. After sampling is complete, the sponge device is returned to the centrifuge tube and screwed in tightly. The tube is then appropriately labeled at the top (two split peel-off labels would eliminate most additional labeling) of the stick and appropriately packed and sent to the laboratory. Upon receipt, the sample is properly recorded and ca. 15–20 mL of double-strength UVM Broth is added to the centrifuge tube to at least partially cover the sponge. The entire system is then incubated at 30° C. for 24 h. After incubation the sponge is gently rotated while pressing against the side of the tube to remove as much UVM Broth as possible and then inserted into a second identical screw-capped centrifuge tube containing a sufficient volume of Fraser Broth (ca. 20 mL) to resaturate the sponge. This tube containing the Fraser Broth enrichment is incubated at 35° C. Following 24 and 48 h of incubation, the sponge device is removed from the centrifuge tube and the pointed tip of the sponge is touched to appropriately labeled plates of MOX and LPM Agar. After the inoculum on both plates is streaked for isolation with a sterile loop, the plates are incubated at 35° C. and examined for Listeria-like colonies after 24 and 48 h of incubation according to the USDA procedure. Colonies resembling Listeria are re-isolated on TSA-YE agar and confirmed as Listeria spp. according to the standard USDA protocol.

Using the newly developed sponge transfer device, recovery of Listeria spp. from food-processing environments is about 35–40% higher than what would be expected using the current USDA procedure. Further, the new sponge transfer device method has a false negative rate of 1.89% as compared to 37.7% for the current USDA procedure (FIG. 2). In addition, the sponge transfer device is faster, easier and more economical to use than the current USDA sponge for the following reasons:

(a) No special external packaging is needed since the sponge device is self-contained inside a sterile non-breakable centrifuge tube.
(b) The sponge transfer device is more convenient to use since it can be handled aseptically above the cap and does not require the use of disposable gloves. The disposable gloves used in the food industry are normally non-sterile. Hence, the new method is more aseptic and offers a lower risk of contamination.
(c) Hard-to-reach corners and crevices can be sampled with relative ease using the pointed end of the sponge transfer device.
(d) A label containing the date, factory name, sample number, sample site and other pertinent information can be directly applied to the top of the sponge transfer device. The fact that no additional labeling is required in the laboratory until the MOX and LPM plates are streaked eliminates the risk of sample mix-ups and labeling errors.
(e) The sponge transfer device is shipped to the laboratory in a non-breakable, leak-proof centrifuge tube as opposed to a thin plastic Whirl-Pak bag that can leak if improperly sealed, punctured or torn.
(f) About 15–20 mL of double strength UVM Broth is needed for proper primary enrichment for the sponge transfer device as opposed to 50 mL of single strength UVM Broth for the currently used USDA sponge.

The numerous advantages just discussed pertain to the use of the newly developed sponge transfer device for recovery of Listeria spp. from food-processing environments. However, this device is also useful for recovery of other environmental contaminants of importance, including Salmonella and Yersinia.

We have determined that Listeria recovery is not proportional to any increase in the volume of sponge contents sampled after enrichment in UVM Broth. Further, when 225 environmental sponge samples were examined for Listeria spp. in accordance with the present invention, a total of 52 samples were positive for Listeria. In contrast, a total of 33 of the same samples were positive for Listeria using the 0.1 mL transfer method. There was only one sample that was detected as being Listeria positive by the standard method but not detected by the sponge method. The sponge method thus resulted in an increase of detection of about 37.7% over the standard method.

We claim:

1. Apparatus for enhancing the recovery and isolation of microorganisms in samples or specimens comprising:
   a. inoculating means for transferring an inoculum from one medium to another medium;
   b. container means for maintaining an enrichment medium and a sample free from outside contaminants, the container means having a top and bottom portion;
   c. positioning means for positioning the inoculating means in a predetermined position relative to the bottom portion of the container means;
   d. first aperture means disposed on the top portion of the container means for introducing a sample and the enrichment medium into the container means;
   e. second aperture means disposed adjacent the first aperture means for introducing the inoculating means into the container means and for securing the positioning means so that the inoculating means is disposed in a predetermined position relative to the bottom portion of the container means; and,
   f. sealing means for sealing the sample, the enrichment medium, and the inoculating means from the outside environment to maintain the sample, the enrichment medium, and the inoculating means in an environment free from outside contaminants.

2. The apparatus of claim 1 in which the positioning means is further provided with streaking means for streaking the inoculum onto plating media.

3. The apparatus of claim 1 in which the inoculating means is made from material selected from the group consisting of natural fibers, synthetic fibers, blends of natural and synthetic fibers, sponge, wood, metal and plastic.

4. The apparatus of claim 3 in which the inoculating means is disposed on one end of a shaft and in which the opposite end of the shaft is secured to a cap.

5. The apparatus of claim 4 in which the cap is adapted to bear written identification.

6. The apparatus of claim 1 in which the sealing means comprises a container closure for the container means, and in which the second aperture means comprises at least one aperture in the container closure.

7. The apparatus of claim 6 in which the inoculating means is disposed on one end of a shaft, and in which the opposite end of the shaft is secured to a cap, and in which the cap is adapted to seal the aperture in the container closure.

8. The apparatus of claim 7 in which the cap is adapted to bear written identification.

9. The apparatus of claim 1 in which the inoculating means is a swab.

10. The apparatus of claim 9 in which the swab is made of material selected from the group consisting of cotton, cotton/synthetic blends and sponge.

11. The apparatus of claim 1 in which the positioning means is an elongated rod formed from material selected from the group consisting of wood, plastic and metal.

12. The apparatus of claim 11 in which the elongated rod is further provided with streaking means for streaking the sample onto selective plating media.

13. The apparatus of claim 1 in which the positioning means is adjustable so that the inoculating means may be extended to be placed in a predetermined position relative to the bottom portion of the container means and contracted to fit in a test tube, where the test tube has a height substantially less than a height of the container means.

14. The apparatus of claim 13 in which the positioning means comprises at least two elongated parts in telescoping relationship secured to cap disposed on the sealing means and in which the inoculating means is disposed on the outermost end of part that extends farthest from the cap.

15. The apparatus of claim 14 in which the elongated parts of the positioning means are adapted to telescopically expand relative to each other to position the inoculating means in a predetermined position relative to the bottom portion of the container means and are further adapted to telescopically contract relative to each other so that the inoculating means and positioning means will fit into a test tube, where the test tube has a height substantially less than the height of the container means.

16. Apparatus for enhancing the recovery and isolation of microorganisms in samples or specimens comprising:
 a. inoculating means for transferring an inoculum from one medium to another medium;
 b. container means for containing an enrichment mediums, a sample, and the inoculating means, the container means having a top and a bottom portions;
 c. positioning means for positioning the inoculating means in a predetermined position relative to the bottom portion of the container means;
 d. first aperture means disposed on the top portion of the container means for introducing the sample and an enrichment medium into the container means;
 e. second aperture means disposed adjacent the first aperture means for introducing the inoculating means into the container means;
 f. cap means for closing the second aperture means and for securing the positioning means so that the inoculating means is disposed in a predetermined position relative to the bottom portion of the container means; and,
 g. closure means for closing the container means to separate the sample, the enrichment medium, and the inoculating means from the outside environment.

17. The apparatus of claim 16 in which the positioning means comprises a shaft.

18. The apparatus of claim 17 in which the inoculating means is a swab.

19. The apparatus of claim 18 in which the swab is made of material selected from the group consisting of natural fibers, synthetic fibers, blends of natural and synthetic fibers, sponge, wood, metal and plastic.

20. The apparatus of claim 19 in which the shaft comprises an elongated rod made from material selected from the group consisting of wood, plastic and metal.

21. The apparatus of claim 20 in which the shaft is further provided with streaking means for streaking the sample onto selective plating media.

22. The apparatus of claim 10 in which the cap means is adapted to include a means for bearing written identification.

23. The apparatus of claim 16 in which the positioning means is adjustable so that the inoculating means may be extended in length to be placed in a predetermined position relative to the bottom portion of the container means and may be contracted in length to fit in a test tube, said test tube having a height substantially less than a height of the container means.

24. The apparatus of claim 23 in which the positioning means comprises at least two elongated parts in telescoping relationship to each other, one part being secured to the cap means, and in which the inoculating means is disposed on the outermost end of part that extends farthest from the cap means.

25. The apparatus of claim 24 in which the at least two elongated parts of the positioning means are adapted to telescopically expand relative each other to position the inoculating means in a predetermined position relative to the bottom portion of the container means and are further adapted to telescopically contract relative to each other so that the inoculating means and shaft will fit into a test tube, where the test tube has a height substantially less than a height of the container means.

26. The apparatus of claim 23 in which the cap is adapted to bear written identification.

27. Apparatus for enhancing the recovery and isolation of contaminants in environmental samples comprising:
 a. a container having a top and a bottom portion;
 b. a sponge for collecting environmental samples from an environmental surface, said sponge having a tapered portion configured to communicate with the bottom portion of the container and configured to enhance said collecting of environmental samples;
 c. the sponge secured to handle means for holding the sponge and for positioning the sponge in a predetermined relationship relative to the bottom portion of the container;

d. sealing means for sealing the contents of the container, including the sponge, in a sterile environment free from outside contaminants.

28. The apparatus of claim 27 in which the container means is a centrifuge tube.

29. The apparatus of claim 28 in which the sponge is a sterilized cellulose sponge configured to fit in the centrifuge tube.

30. The apparatus of claim 29 in which the handle means is a plastic rod.

31. The apparatus of claim 27 in which the sealing means is a cap secured to the handle means and adapted to form a barrier between a portion of the handle means to be held by hand and the portion of the handle means to which the collection means is attached.

32. The apparatus of claim 31 in which label means for labeling the apparatus are secured to the handle means.

* * * * *